(12) United States Patent
Zuo et al.

(10) Patent No.: US 12,685,433 B2
(45) Date of Patent: Jul. 21, 2026

(54) ENDOSCOPE IMAGING SYSTEM, LIGHT SOURCE CONTROL METHOD THEREOF, AND COMPUTER READABLE STORAGE MEDIUM

(71) Applicants: WUHAN MINDRAY SCIENTIFIC CO., LTD., Wuhan City (CN); SHENZHEN MINDRAY BIO-MEDICAL ELECTRONICS CO., LTD., Shenzhen (CN)

(72) Inventors: Pengfei Zuo, Shenzhen (CN); Cheng Fan, Shenzhen (CN); Ruiling Pan, Shenzhen (CN); Chenghua Huang, Shenzhen (CN)

(73) Assignees: Wuhan Mindray Scientific Co., Ltd., Wuhan City (CN); Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 18/745,599

(22) Filed: Jun. 17, 2024

(65) Prior Publication Data

US 2024/0415378 A1    Dec. 19, 2024

(30) Foreign Application Priority Data

Jun. 19, 2023    (CN) .......................... 202310735711.2

(51) Int. Cl.
*G06T 7/11*        (2017.01)
*A61B 1/00*        (2006.01)
(Continued)

(52) U.S. Cl.
CPC ........ *A61B 1/0661* (2013.01); *A61B 1/00004* (2013.01)

(58) Field of Classification Search
CPC . A61B 1/0661; A61B 1/00004; A61B 1/0004; A61B 1/00006; A61B 1/00009;
(Continued)

(56) References Cited

U.S. PATENT DOCUMENTS 6,635,011 B1 * 10/2003 Ozawa ............... A61B 1/00096
                                                  348/E5.029
12,020,420 B2 * 6/2024 Saito ................... A61B 5/02007
(Continued)

FOREIGN PATENT DOCUMENTS

CN        112689469 A        4/2021
CN        115956869 A        4/2023
(Continued)

OTHER PUBLICATIONS

Extended European Search Report dated Feb. 17, 2025, issued in related European Patent Application No. 24182969.6 (14 pages).
(Continued)

*Primary Examiner* — Howard D Brown, Jr.
(74) *Attorney, Agent, or Firm* — Sheppard Mullin Richter & Hampton LLP

(57)        ABSTRACT

An endoscope imaging system, and a control method for a light source of an endoscope imaging system, are disclosed. After a function key is triggered, the image processing unit controls the light source unit to perform a first function, and controls the endoscope imaging system to perform a second function which corresponds to the function key. Alternatively, the image processing unit controls the light source unit to perform a first function, after the function key is triggered; and controls the endoscope imaging system to perform a second function which corresponds to the function key, after the function key is re-triggered. This disclosure provides another completely different way to control the light source unit to perform the first function, so as to (Continued)

achieve functional linkage of various units in the endoscope imaging system, simplify operation steps, and improve surgical efficiency.

19 Claims, 3 Drawing Sheets

(51) Int. Cl.
    *A61B 1/06*           (2006.01)
    *H04N 7/18*           (2006.01)

(58) Field of Classification Search
    CPC ..... A61B 1/0005; A61B 1/00194; A61B 1/04;
                A61B 1/043; A61B 1/045; A61B 1/0638;
                A61B 1/0655; A61B 1/00045; A61B 1/07
    See application file for complete search history.

(56) References Cited

U.S. PATENT DOCUMENTS

| | | | | |
|---|---|---|---|---|
| 2002/0045801 A1* | 4/2002 | Niida | .................. | A61B 1/00055 |
| | | | | 600/118 |
| 2002/0118278 A1* | 8/2002 | Kobayashi | ............. | G16H 30/20 |
| | | | | 382/130 |
| 2002/0196335 A1* | 12/2002 | Ozawa | ................... | H04N 23/88 |
| | | | | 348/E9.052 |
| 2003/0030722 A1* | 2/2003 | Ozawa | ................... | H04N 23/88 |
| | | | | 348/71 |
| 2003/0076412 A1* | 4/2003 | Ozawa | ................... | H04N 23/88 |
| | | | | 348/65 |
| 2013/0016200 A1 | 1/2013 | Ovod | | |
| 2014/0018622 A1 | 1/2014 | Hoeg et al. | | |
| 2017/0100018 A1* | 4/2017 | Saito | ...................... | G02B 23/24 |
| 2018/0184881 A1 | 7/2018 | Urasaki et al. | | |
| 2018/0338675 A1 | 11/2018 | Eggli et al. | | |
| 2023/0016855 A1 | 1/2023 | Endo | | |
| 2024/0061547 A1* | 2/2024 | Fleizach | ............. | G06F 3/04815 |

FOREIGN PATENT DOCUMENTS

| | | |
|---|---|---|
| JP | 2001-112711 A | 4/2001 |
| JP | 2011-072384 A | 4/2011 |
| JP | 32-09297 U | 3/2017 |

OTHER PUBLICATIONS

First Office Action and Search Report dated Jun. 12, 2026, issued in Chinese Patent Application No. 202310735711.2, with English machine translation (32 pages).

\* cited by examiner

201

Obtaining an image signal generated based on an image light; wherein the image light is reflected and/or excited by an region to be observed, after illuminating, by the image acquisition unit, the region to be observed with an illumination light provided by the light source unit

202

Processing the image signal to output a display signal

203 controlling the light source unit to perform a first function, after the function key is triggered; and further controlling to perform a second function which corresponds to the function key, after the function key is re-triggered; wherein the second function is different from the first function

FIG. 5

301

Obtaining an image signal generated based on an image light; wherein the image light is reflected and/or excited by an region to be observed, after illuminating, by the image acquisition unit, the region to be observed with an illumination light provided by the light source unit

302

Processing the image signal to output a display signal

303

If the light source unit does not provide the illumination light; performing, by the image processing unit, image recognition based on the image signal which is obtained from the image acquisition unit, and controlling the light source unit to perform a first function, when an image recognition result is determined to satisfy a preset scenario; wherein the first function comprises at least one of: turning on the light source unit and providing the illumination light

FIG. 6

ENDOSCOPE IMAGING SYSTEM, LIGHT SOURCE CONTROL METHOD THEREOF, AND COMPUTER READABLE STORAGE MEDIUM

CROSS-REFERENCE TO RELATED APPLICATIONS

This disclosure is based on and claims priority to and benefits of Chinese patent Application No. 202310735711.2, filed on Jun. 19, 2023. The entire content of the above-referenced application is incorporated herein by reference.

TECHNICAL FIELD

The disclosure relates to an endoscope technical field, more specifically, relates to an endoscope imaging system, a control method for a light source of an endoscope imaging system, and a computer-readable storage medium.

BACKGROUND

At present, an endoscope imaging system in clinical practice usually uses functions provided by a light source during surgical preparation and operation, which functions are usually assisted by a touring nurse or an assistant. For example, a turning-on operation of the light source is usually started through triggering a corresponding key at a host of a light source by the touring nurse. If the touring nurse is busy or the assistant is not familiar with the operation, the surgical progress is to be delayed, the surgical efficiency is to be reduced, and especially the inconvenience of use in very busy preoperative situations, is to be increased.

SUMMARY

An embodiment of this disclosure provides an endoscope imaging system, a control method for a light source of an endoscope imaging system, and a computer-readable storage medium, which are capable of providing another completely different way to control a light source unit to perform certain functions, so as to achieve functional linkage of various units in the endoscope imaging system, simplify operation steps, and improve surgical efficiency.

On one hand, an embodiment of this disclosure provides an endoscope imaging system, including: an image acquisition unit, an image processing unit, a light source unit, and a function key;

the light source unit is configured to provide an illumination light;

the image acquisition unit is configured to receive the illumination light which is provided by the light source unit and illuminate a region of a patient to be observed with the illumination light, and acquire an image light which is reflected and/or excited by the region to be observed and generate an image signal based on the image light;

the image processing unit is in signal connection with the image acquisition unit;

wherein the image processing unit is configured to obtain the image signal from the image acquisition unit, and process the image signal to output a display signal;

the image processing unit is further in signal connection with the light source unit;

wherein after the function key is triggered, the image processing unit is further configured to control the light source unit to perform a first function which corresponds to the function key, and control the endoscope imaging system to perform a second function which also corresponds to the function key;

wherein the first function includes at least one of: turning on the light source unit, and providing the illumination light; the second function includes one or more of: photographing, video recording, white balance, auto-focus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, turning on and off a smoke exhaust.

In an embodiment, the first function is performed before the second function.

In an embodiment, the first function is: after the light source unit is turned on, providing the illumination light at a first preset brightness value without delay.

In an embodiment, the function key is a key for white balance, and the second function is a function for image white balance of the endoscope imaging system.

In an embodiment, the first function is: after the light source unit is turned on, providing the illumination light which is provided by the light source unit, with a brightness value thereof being controlled to increase from zero or a first preset brightness value to a second preset brightness value within a preset time length.

In an embodiment, the first function is: after the light source unit is turned on, providing the illumination light which is provided by the light source unit, with a brightness value thereof being controlled to increase from zero or a first preset brightness value to a second preset brightness value within a preset time length, in a linear or nonlinear manner or with a predetermined step.

In an embodiment, the function key is any function key which is not a key for white balance.

In an embodiment, the function key is triggered based on a manual operation of a user; or the function key is triggered based on a recognition result of the image signal, which signal is obtained by the image processing unit, if the light source unit does not provide the illumination light.

In an embodiment, the function key includes at least one of: a physical function key which is arranged at the image acquisition unit, a physical function key which is arranged at the image processing unit, and a virtual function key which is displayed on a graphic user interface of the image processing unit.

In an embodiment, the function key includes combination key(s), which include(s) multiple keys; wherein the combination key(s) is (are) triggered, after the multiple keys are operated by a user according to a preset rule.

On the other hand, an embodiment of this disclosure also provides another endoscope imaging system, including: an image acquisition unit, an image processing unit, a light source unit, and a function key;

the light source unit is configured to provide an illumination light;

the image acquisition unit is configured to receive the illumination light which is provided by the light source unit and illuminate a region of a patient to be observed with the illumination light, and acquire an image light which is reflected and/or excited by the region to be observed and generate an image signal based on the image light;

the image processing unit is in signal connection with the image acquisition unit;

3 wherein the image processing unit is configured to obtain the image signal from the image acquisition unit, and process the image signal to output a display signal;

wherein the image processing unit is further in signal connection with the light source unit; wherein the image processing unit is further configured to control the light source unit to perform a first function which corresponds to the function key, after the function key is triggered; and to further control the endoscope imaging system to perform a second function which also corresponds to the function key, after the function key is re-triggered; wherein the first function includes at least one of: turning on the light source unit, and providing the illumination light; the second function is different from the first function.

In an embodiment, the function key is triggered based on a first operation of a user, so as to perform the first function; the function key is re-triggered based on a second operation of a user, so as to perform the second function.

In an embodiment, the first operation is long-pressing the function key by the user, the second operation is short-pressing the function key by the user.

In an embodiment, the function key is a key for white balance; the first function is: after the light source unit is turned on, providing the illumination light at a first preset brightness value without delay; and the second function is a function for image white balance of the endoscope imaging system.

In an embodiment, the first function is: after the light source unit is turned on, providing the illumination light which is provided by the light source unit, with the brightness value thereof being controlled to increase from zero or the first preset brightness value to the second preset brightness value within the preset time length, in a linear or nonlinear manner or with a predetermined step; wherein the first preset brightness value is smaller than the second preset brightness value; the function key is any function key which is not a key for white balance.

In an embodiment, the second function includes one or more of: photographing, video recording, white balance, autofocus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, turning on and off a smoke exhaust.

On the other hand, an embodiment of this disclosure also provides another endoscope imaging system, including: an image acquisition unit, an image processing unit, a light source unit, and a function key;

the light source unit is configured to provide an illumination light;

the image acquisition unit is configured to receive the illumination light which is provided by the light source unit and illuminate a region of a patient to be observed with the illumination light, and acquire an image light which is reflected and/or excited by the region to be observed and generate an image signal based on the image light;

the image processing unit is in signal connection with the image acquisition unit; wherein the image processing unit is configured to obtain the image signal from the image acquisition unit, and process the image signal to output a display signal;

wherein the image processing unit is further in signal connection with the light source unit; wherein the image processing unit is further configured to perform image recognition based on the image signal which is obtained from the image acquisition unit, if the light source unit does not provide the illumination light, and to control the light source unit to perform a first function, when determining that an image recognition result satisfies a preset scenario; wherein the first function includes at least one of: turning on the light source unit, and providing the illumination light.

On the other hand, an embodiment of this disclosure also provides a control method for a light source of an endoscope imaging system, wherein the endoscope imaging system includes: an image acquisition unit, an image processing unit, a light source unit, and a function key;

wherein the control method incudes:

obtaining, by the image processing unit, an image signal which is generated based on an image light; wherein the image light is reflected and/or excited by a region of a patient to be observed, after illuminating, by the image acquisition unit, the region to be observed with an illumination light which is provided by the light source unit;

processing, by the image processing unit, the image signal to output a display signal;

wherein the control method further includes:

after the function key is triggered, controlling the light source unit to perform a first function which corresponds to the function key, and further controlling the endoscope imaging system to perform a second function which also corresponds to the function key; wherein the first function includes at least one of: turning on the light source unit, and providing the illumination light; the second function is different from the first function.

On the other hand, an embodiment of this disclosure also provides a control method for a light source of an endoscope imaging system, wherein the endoscope imaging system includes: an image acquisition unit, an image processing unit, a light source unit, and a function key;

wherein the control method includes:

obtaining, by the image processing unit, an image signal which is generated based on an image light; wherein the image light is reflected and/or excited by a region of a patient to be observed, after illuminating, by the image acquisition unit, the region to be observed with an illumination light which is provided by the light source unit;

processing, by the image processing unit, the image signal to output a display signal;

wherein the control method further includes:

controlling the light source unit to perform a first function which corresponds to the function key, after the function key is triggered; and further controlling the endoscope imaging system to perform a second function which also corresponds to the function key, after the function key is re-triggered; wherein the first function includes at least one of: turning on the light source unit, and providing the illumination light; the second function is different from the first function.

On the other hand, an embodiment of this disclosure also provides a control method for a light source of an endoscope imaging system, wherein the endoscope imaging system includes: an image acquisition unit, an image processing unit, a light source unit, and a function key;

wherein the control method includes:

obtaining, by the image processing unit, an image signal which is generated based on an image light; wherein the image light is reflected and/or excited by a region of a patient to be observed, after illuminating, by the image acquisition unit, the region to be observed with an illumination light which is provided by the light source unit;

processing, by the image processing unit, the image signal to output a display signal;

wherein the control method further includes:

performing, by the image processing unit, image recognition based on the image signal which is obtained from the image acquisition unit, if the light source unit does not provide the illumination light; and controlling the light source unit to perform a first function, when an image recognition result is determined to satisfy a preset scenario; wherein the first function includes at least one of: turning on the light source unit, and providing the illumination light.

On the other hand, an embodiment of this disclosure also provides a computer-readable storage medium, wherein the computer-readable storage medium stores computer program(s) which is (are) suitable for loading to a processor, so as to perform steps of any one control method for a light source of an endoscope imaging system described above.

On the other hand, an embodiment of this disclosure also provides another endoscope imaging system, including: an image acquisition unit, an image processing unit, a light source unit, and a function key;

the light source unit is configured to provide an illumination light;

the image acquisition unit is configured to receive the illumination light which is provided by the light source unit and illuminate a region of a patient to be observed with the illumination light, and acquire an image light which is reflected and/or excited by the region to be observed and generate an image signal based on the image light;

the image processing unit is in signal connection with the image acquisition unit;

wherein the image processing unit is configured to obtain the image signal from the image acquisition unit, and process the image signal to output a display signal;

wherein the image processing unit is further in signal connection with the light source unit; wherein the image processing unit is further configured to control the light source unit to perform a first function, and control the endoscope imaging system to perform a second function which corresponds to the function key, after the function key is triggered; wherein the first function is different from the second function.

In an embodiment, the first function is: after the light source unit is turned on, providing the illumination light at a first preset brightness value without delay.

In an embodiment, the function key is a key for white balance, and the second function is a function for image white balance of the endoscope imaging system.

In an embodiment, the first function is: after the light source unit is turned on, providing the illumination light which is provided by the light source unit, with a brightness value thereof being controlled to increase from zero or a first preset brightness value to a second preset brightness value within a preset time length.

In an embodiment, the function key is any function key which is not a key for white balance.

In embodiments of this disclosure, an image processing unit and a light source unit inside an endoscopic imaging system are in signal connection. After a function key of the endoscopic imaging system is triggered, the image processing unit controls the light source unit to perform a first function which corresponds to the function key, wherein the first function includes at least one of: turning on the light source unit, and providing the illumination light; and controls the endoscope imaging system to perform a second function which also corresponds to the function key, wherein the second function includes one or more of: photographing, video recording, white balance, autofocus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, turning on and off a smoke exhaust. By the triggering of the function key, the light source can be controlled to perform the first function which corresponds to the function key, and the endoscope imaging system can be controlled to perform the second function which also corresponds to the function key. For example, through operating one key once by the user (when a triggering of the function key is defined as operating a certain key by the user), not only can the light source be controlled to perform the first function which corresponds to the function key, but also the endoscope imaging system can be controlled to perform the second function which also corresponds to the function key, avoiding the problem of low operation efficiency caused by multiple operations. At the same time, such operation also avoids the problems of affecting the surgical progress, which problems are caused by that the touring nurse is busy before surgery or the assistant is not familiar with the operation, and improves surgical efficiency.

Alternatively, after the function key of the endoscope imaging system is triggered, the light source unit is controlled to perform a first function which corresponds to the function key, wherein the first function includes at least one of: turning on the light source unit, and providing the illumination light. After the function key of the endoscope imaging system is re-triggered, the endoscope imaging system is controlled to perform a second function which also corresponds to the function key; wherein the second function is different from the first function. In this way, the light source unit is controlled to perform the first function by one function key, and the second function which corresponds to the function key can be achieved after the same function key is re-triggered, which improves surgical efficiency.

Alternatively, if the light source unit does not provide the illumination light, image recognition is performed based on the image signal which is obtained from the image acquisition unit, and when determining that an image recognition result satisfies a preset scenario, the light source unit is controlled to perform a first function, which includes at least one of: turning on the light source unit, and providing the illumination light. Accordingly, the light source unit is controlled to automatically perform the first function without requiring manual operation, which improves surgical efficiency.

In the above embodiments, certain functions provided by the light source unit are perform through a function key or image recognition, which provides another completely different way to control a light source unit to perform certain functions, so as to achieve functional linkage of various units in the endoscope imaging system, simplify operation steps, and improve surgical efficiency.

BRIEF DESCRIPTION OF THE DRAWINGS

In order to more clearly explain the embodiments of this disclosure, the following briefly introduces the drawings which are needed to be used in the description of the embodiments. It is obvious that the drawings in the following description are only some embodiments of this disclosure. For those skilled in the art, other drawings can be obtained from these accompanying drawings without paying any creative works.

FIG. 5 is a flowchart of a control method for a light source of an endoscope imaging system provided in another embodiment of this disclosure.

FIG. 6 is a flowchart of a control method for a light source of an endoscope imaging system provided in a further embodiment of this disclosure.

DESCRIPTION OF THE PREFERRED EMBODIMENTS

The technical solutions in the embodiments of this disclosure are described clearly and completely below in combination with the drawings in the embodiments of this disclosure. Obviously, the described embodiments are just some of the embodiments of this disclosure, not all of them. According to the embodiments in this disclosure, all other embodiments obtained by those skilled in the art without making creative work fall within the protection scope of this disclosure.

Figure 1:
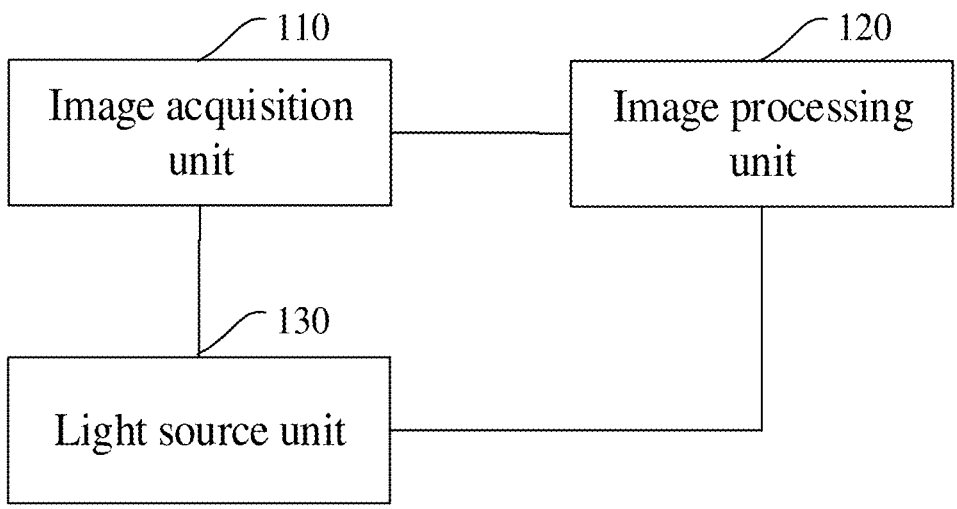
FIG. 1 is a structural diagram of an endoscope imaging system provided in an embodiment of this disclosure.
Figure 2:
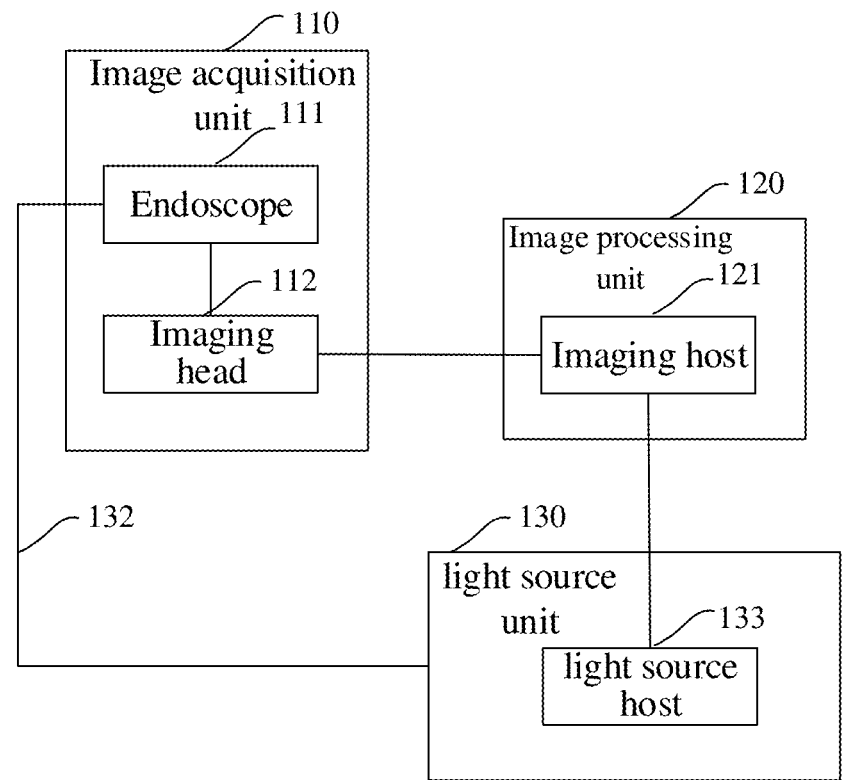
FIG. 2 is a structural diagram of an endoscope imaging system provided in another embodiment of this disclosure.

FIG. 1 is a structural diagram of an endoscope imaging system provided in an embodiment of this disclosure. FIG. 2 is a structural diagram of an endoscope imaging system provided in another embodiment of this disclosure. Please refer to the endoscope imaging system in an embodiment of this disclosure in conjunction with FIGS. 1 and 2.

As shown in FIG. 1, the endoscope imaging system includes an image acquisition unit 110, an image processing unit 120, and a light source unit 130. Wherein the image acquisition unit 110 is connected with the light source unit 130, for example, through connection of a light guide beam, so as to enable the image acquisition unit 110 to acquire an illumination light provided by the light source unit 130. The image processing unit 120 is in signal connection with the image acquisition unit 110, and the image processing unit 120 is further in signal connection with the light source unit 130, such as in wired connection or wireless connection, as long as a communication control between these units can be achieved. The endoscope imaging system also includes at least one function key, that is, at least one function key is also arranged inside the endoscope imaging system. In an embodiment, the endoscopic imaging system further includes a display unit, such as at least one display.

Wherein, the light source unit 130 is configured to provide an illumination light. The illumination light provided by the light source unit 130 includes a visible illumination light and/or an excitation light, such as an excitation light which corresponds to (fluorescent) dyes (such as a near-infrared light), etc. The excitation light can be a visible light or an invisible light, and its specific wavelength range depends on a used fluorescent agent.

As shown in FIG. 2, in some embodiments, the endoscopic imaging system further includes a light guide beam 132, and the light source unit 130 transmits the provided illumination light to the image acquisition unit 110 through the light guide beam 132.

The image acquisition unit 110 is configured to receive the illumination light provided by the light source unit 130 and illuminate a region of a patient to be observed with the illumination light, and acquire an image light, which is reflected and/or excited by the region of the patient to be observed and generate an image signal based on the image light.

As shown in FIG. 2, in some embodiments, the image acquisition unit 110 includes an endoscope 111 and an imaging head 112.

Wherein, the endoscope 111 is connected with the light source unit 130, for example, through the light guide beam 132. One end of the light guide beam 132 is connected with the light source unit 130, and the other end of the light guide beam 132 is connected with the endoscope 111. The light emitted by the light source unit 130 can enter the endoscope 111 through the light guide beam 132 and exit from an inserted head end of the endoscope 111.

The endoscope 111 is configured to receive the illumination light transmitted by the light source unit 130 and illuminate the region of the patient to be observed with the illumination light, as well as, to obtain the image light, which is reflected and/or excited by the region to be observed. If the light source unit 130 provides a visible illumination light, then the image light, which is reflected by the region to be observed, can be obtained. If the light source unit 130 provides a fluorescence excitation light, then the image light, which is excited by a dye at the region to be observed, can be obtained. If the light source unit 130 provides both visible illumination light and fluorescence excitation light, then the image light which reflected by the region to be observed and the image light which excited by the dye, are simultaneously obtained.

Wherein, the imaging head 112 is connected with the endoscope 111 and is configured to obtain the image light which is reflected and/or excited by the region of the patient to be observed, and generate an image signal based on the image light. The imaging head 112 is further in signal connection with the image processing unit 120 for transmitting the image signal to the image processing unit 120.

For optical hard endoscopic, the image acquisition unit 110 can include an endoscope 111 and an imaging head 112, which can be detachably connected through an optical bayonet mount. The imaging head 112 is arranged inside with an image sensor to convert the image light into the image signal.

When the endoscope 111 is an optical hard endoscopic, one end of the light guide beam 132 is connected with the light source unit 130, and the other end of the light guide beam 132 is connected with an interface of the endoscope 111 for the light guide beam. The endoscope 111 also includes an imaging head interface, which is connected a bayonet mount of the imaging head 112, such as a bayonet mount at a head portion of the imaging head 112. The imaging head 112 is also connected with the image processing unit 120, such as through a cable at a tail portion of the imaging head 112. The imaging head 112 includes one or more image sensors, and the endoscope 111 is mainly used to transmit the image light to the imaging head 112. The image sensor in the imaging head 112 converts a light signal which corresponds to the image light into an electrical signal, so as to form the image signal. At the same time, the imaging head 112 also serves as a component for a gripping operation, and its handle is correspondingly arranged with physical function key(s) for the imaging head.

For 3D electronic hard endoscopic, the image acquisition unit 110 usually includes a hard endoscopic as an insertion part and a handle as a gripping part, both of which are an integrated structure. The image sensor is arranged at the head end of the hard endoscopic, and only a portion of an image signal processing board and a key control board are arranged inside the handle.

For 3D electronic hard endoscopic, the insertion part and handle are an integrated structure, and the light guide beam which connects the light source unit 130 and the cable which transmits the image signal are arranged at a side of the 3D hard endoscopic, which side is away from the insertion part. Physical function key(s) can be arranged at the handle.

Wherein, the corresponding endoscopic in the optical hard endoscopic and 3D electronic hard endoscopic are hard. One difference between an electronic soft endoscopic and the 3D electronic hard endoscopic is that an insertion part of the electronic soft endoscopic is a soft structure.

It should be noted that an embodiment of this disclosure can be applicable to different types of endoscopic products, and the above is only for illustration purposes.

The image processing unit 120 is configured to obtain an image signal from the image acquisition unit 110 and process the image signal to output a display signal. This display signal is configured to display, on the display unit, an image of the region of the patient to be observed.

In an embodiment, the image processing unit 120 may include an independent imaging host 121.

As shown in FIG. 2, in an embodiment, the light source unit 130 may include an independent light source host 133. Among them, the imaging host 121 is in signal connection with the light source host 133. The imaging host 121 transmits corresponding instruction(s) to the light source host 133, so as to control the light source host 133 to perform certain function(s).

In an embodiment shown in FIG. 2, the imaging host 121 and the light source host 133 exist independently. In other embodiments, the imaging host and the light source host are in a form of an integrated device, which achieves both the functions of the imaging host and the light source host through a single device. Therefore, the image processing unit 120 and the light source unit 130 mentioned in an embodiment of this disclosure can be implemented by an integrated device, or by two independent devices.

In an embodiment, the endoscope imaging system further includes a display unit, such as a display. The display unit is connected with the image processing unit 120 for displaying the image signal, that is, displaying an imaged image.

The display unit is configured to receive the display signal from the imaging host 121 and display the imaged image based on the display signal. One end of a video connection cable is connected with a video output interface of the imaging host 121, and the other end of the video connection cable is connected with a video input interface of the display screen.

In some embodiments, for abdominal surgery scenarios, the endoscope imaging system may further include a pneumoperitoneum machine, a power cord for the pneumoperitoneum machine, a gas supply pipe, and a pneumoperitoneum pipe.

Wherein, the pneumoperitoneum machine is configured to inflate an abdominal cavity of the patient for convenience of doctor during surgery. One end of the gas supply pipe is connected with a carbon dioxide outlet in an operating room, the other end of the gas supply pipe is connected with a gas inlet of the pneumoperitoneum machine, one end of the pneumoperitoneum pipe is connected with a gas outlet of the pneumoperitoneum machine, and the other end of the pneumoperitoneum pipe is connected with the abdominal cavity of the patient. After all the above devices are connected and working properly, the endoscope 111 can be inserted into the body of the patient to observe the condition of the patient from a display screen.

In an embodiment, the image processing unit 120 is in signal connection with the light source unit 130. The image processing unit 120 is further configured to control the light source unit 130 to perform a first function after the function key is triggered, as well as to control the endoscope imaging system to perform a second function which also corresponds to the function key; wherein, the first function and the second function are different.

In an embodiment, the first function includes at least one of: turning on the light source unit, and providing the illumination light; the second function includes one or more of: photographing, video recording, white balance, autofocus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, turning on and off a smoke exhaust.

Wherein, functions, such as photographing, video recording, white balance, autofocus, and timer starting, are same as those in existing technology and are not explained again. The function of mode cycling refers to a function of switching between different modes, such as switching between a white light mode and a fluorescence mode. In the white light mode, a visible light (such as white light) is used as the illumination light, while in the fluorescence mode, an excitation light is used as the illumination light. The function of electronic zooming can also be understood as an electronic focal-length adjustment function. After using the function of electronic zooming, from the image which is obtained by the image acquisition unit 110, a smaller range but cleared details can be watched, when comparing with not performing the function of electronic zooming. The function of brightness adjustment(s) for white light(s) refers to a function of adjusting a brightness of the image acquired by the image acquisition unit 110 in the white light mode, and the function of brightness adjustment(s) for fluorescence(s) refers to a function of adjusting a brightness of the image acquired by the image acquisition unit 110 in the fluorescent mode. The function of 3D/2D switching refers to switching between a 3D observation mode and a 2D observation mode. The image observed in 3D observation mode is a 3D image, while the image observed in 2D observation mode is a 2D image. The function of selection(s) for external input source(s) refers to an ability to select external input device(s), which is (are) connected with the endoscope imaging system. The function of spectral coloring switching refers to a function of processing red, green, and blue spectra of an image obtained by the image acquisition unit 110 to highlight a lesion. The function of turning on and off a pneumoperitoneum machine refers to a function of turning on or off the pneumoperitoneum machine, and the function of turning on and off a smoke exhaust refers to a function of turning on and off the smoke exhaust, when the pneumoperitoneum machine is turned on.

For example, after the function key is triggered, a corresponding first instruction is transmitted to the light source unit 130 to control the light source unit 130 to perform the first function (such as turning on the light source unit). In additional, a corresponding second instruction is transmitted to the image acquisition unit 110, such as the imaging head 112, to control the imaging head 112, so as to perform the second function which corresponds to the function key (such as autofocus). Alternatively, the image processing unit 120 can be controlled to perform a second function (such as a function for image white balance).

In some embodiments, the first function is a function that can only be performed by the light source unit 130, such as controlling the light source unit 130 to be turned on, etc. The second function is a function which original corresponds to the function key in the endoscopic imaging system.

After the function key is triggered, the first and second functions are directly controlled to be performed. The function key can be understood as a shortcut key for performing the corresponding functions. For example, after the function key is triggered, the light source unit is controlled to directly perform the first function, and the endoscope imaging system is controlled to directly perform the second function without entering an interface menu for selection.

The function key can be any key at the endoscope imaging system, for example, the function key can be a physical function key arranged at the image acquisition unit 110 (such as the imaging head 112). Alternatively, the function key can be a physical function key of the image processing unit 120 (such as the imaging host 121) and/or a virtual function key displayed on a graphic user interface. The function key includes at least one of a physical function key which is arranged at the image acquisition unit 110, a physical function key which is arranged at the image processing unit 120, and a virtual function key which is displayed on a graphic user interface of the image processing unit 120, a virtual function key which is displayed on a graphic user interface of the imaging host 121. For the virtual function key which is displayed on a graphic user interface of the imaging host 121, this virtual function key can be a virtual function key which corresponds to a physical key at the imaging head 112, or a function key of the imaging host 121 itself. In an embodiment, the physical function key and the virtual function key can be in one-to-one correspondence. For example, the physical function key arranged at the imaging head 112 for performing the function for image white balance, corresponds to the virtual function key for performing the function for image white balance, wherein triggering the physical function key and triggering the virtual function key can perform the same function.

The function key of the imaging head 112 can be an independent key, or combination key(s), which include(s) multiple keys; the combination key(s) is (are) triggered, after the multiple keys are operated by a user according to a preset rule.

In an embodiment, the endoscope imaging system triggers the function key based on a manual operation of the user, or triggers the function key based on speech recognition, or triggers the function key based on recognition of the image signal. For example, the function key can be triggered by long-pressing the function key by the user, short-pressing the function key by the user, or double short-pressing the function key by the user.

For example, the function key can be triggered by long-pressing the physical function key arranged at the imaging head 112 or double short-pressing the virtual function key displayed on the graphic user interface.

In an embodiment, if the light source unit does not provide the illumination light, the function key is triggered based on an image recognition result for the image signal which is obtained by the image processing unit. For example, when the image processing unit 120 recognizes that an image, which corresponds to the image signal, includes a calibration version/standard version, based on the image signal which is obtained by the image acquisition unit 110, the function key is automatically triggered. For example, in white balance adjustment, it is usually necessary to point the endoscope towards white gauze, which enables the image signal recognition. When the white gauze is recognized, the function key is automatically triggered to perform a function of turning on the light source unit (providing a required illumination light for white balance function) and a function for image white balance. It should be noted that when the light source unit does not provide the illumination light, the image acquisition unit can still obtain an image signal due to a presence of ambient light. But at this point, said image signal should be distinguished from a normal surgical image signal, which is obtained when the light source unit provides the illumination light.

When the function key includes combination key(s), wherein the combination key(s) is (are) triggered, after the multiple keys are operated by a user according to a preset rule, so as to perform the first and second functions. For example, the combination key(s) can be triggered simultaneously or in a preset order. If the combination key(s) include(s) two keys, the function key can be triggered by simultaneously short-pressing both keys, or long-pressing one key and then short-pressing the other key, or in other ways.

Correspondingly, by triggering a function key, such as operating the physical key at the image acquisition unit 110 to trigger the function key, the light source unit 130 can be controlled to perform the first function, as well as the endoscope imaging system can be controlled to perform the second function which corresponds to the function key. This provides a completely different way to control the light source unit 130 to perform the first function, achieves performing of two functions by the function key which is triggered, and achieves functional linkage in the endoscope imaging system, thus simplifying operations and improving surgical efficiency.

In an embodiment, the first function and the second function are linked functions with a related relationship. The performing of the first function or of the second function depends on the performing of another function. For example, the performing of the first function requires the performing of the second function as a prerequisite, or the performing of the second function requires the performing of the first function as a prerequisite (i.e., the first function is performed before the second function).

In some embodiments, the first function is performed before the second function. For example, when the second function is a function for image white balance of the endoscope imaging system, in order to correctly complete the function for image white balance, the light source unit must be turned on and the illumination light provided by the light source unit must be at an appropriate brightness value. Therefore, it is necessary to firstly perform the first function, which is controlling the light source unit to be turned on, and controlling the brightness value provided by the light source unit to reach a first preset brightness value. After completing the first function, the second function is performed, that is, the first function is performed before the second function.

In existing technology, for the operation of turning on the light source unit 130 in clinical practice, it is usually the responsibility of the touring nurse or the assistant to turn on the light source unit at a host end of the light source unit. If the touring nurse is busy or the assistant is not familiar with the operation, the surgical progress is delayed.

In an embodiment, after the image processing unit 120 is in signal connection with the light source unit 140, and the function key is triggered, the light source unit 130 is controlled to perform the first function, and the endoscopic imaging system is controlled to perform the second function which corresponds to the function key. The first function is controlling the light source unit 130 to be turned on. After the light source unit 130 is controlled to be turned on, the second function which corresponds to the function key is performed. For example, the second function can be starting video recording, and correspondingly, after the light source unit 130 is controlled to be turned on, the image processing unit 120 can be controlled to perform video recording. In this way, by simply the function key is triggered, the light source unit 130 can be controlled to be turned on, and the second function which corresponds to the function key can be performed, avoiding the problem of delaying the surgical progress, due to that the touring nurse is busy or the assistant is not familiar with the operation, and improves surgical efficiency.

In an embodiment, the image processing unit 120 controls the light source unit 130 to perform a first function of turning on the light source unit 130 and providing the illumination light at a first preset brightness value without delay, after the light source unit 130 is turned on. In this embodiment, the first function is controlling the light source unit 130 to be turned on, such as controlling the light source unit 130 to be turned on and immediately emit strong light after the light source unit 130 is turned on.

Figure 3:
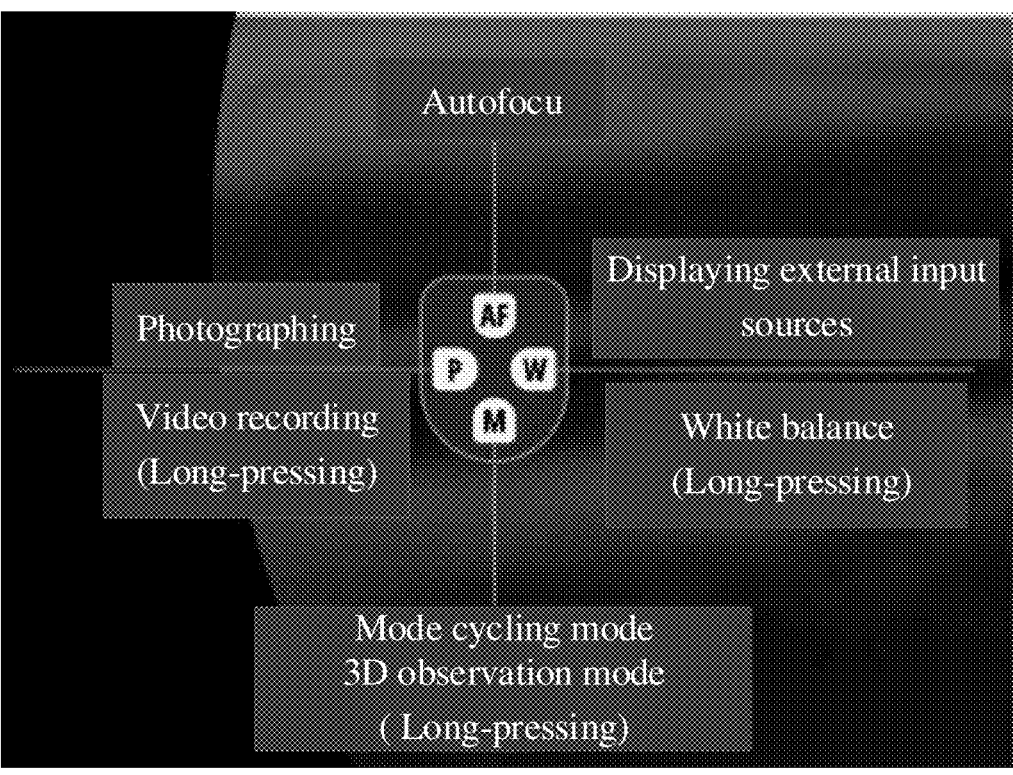
FIG. 3 is a structural diagram of a function key in an endoscope imaging system provided in an embodiment of this disclosure.

As shown in FIG. 3, it is a diagram of function keys provided in the endoscope imaging system in an embodiment. Specifically, FIG. 3 provides function keys of the imaging head 112 of the image acquisition unit 110. The function keys of imaging head 112 include four keys, namely AF (autofocus), P (short-pressing for photographing, long-pressing for video recording), M (short-pressing for entering a mode cycling mode, long-pressing for entering 3D observation mode), and W (short-pressing for displaying external input sources, long-pressing for image white balance). It should be noted that FIG. 3 is only an example, and the function keys of imaging head 112 may include fewer or more. FIG. 3 does not constitute a limitation on the function keys of imaging head 112 in the endoscopic imaging system.

From FIG. 3, it can be seen that the function keys of the imaging head 112 of the endoscope imaging system include the function for image white balance. In the actual use of the medical endoscope imaging system, the function for image white balance is a routine operation at the beginning of clinical surgery, which can ensure that after replacing the endoscope 111 of the endoscope imaging system, the image color is correct. To achieve correct image white balance, the light source unit 130 must be in a state where the light is turned on and the brightness is at an appropriate value.

At present, operating the function for image white balance and turning on the light source unit are two steps in the existing endoscope imaging system. The light source unit is usually turned on by a touring nurse at the light source host. After the light source unit is turned on, the assistant needs to align lens of the hard endoscope with a piece of white gauze. The starting of the function for image white balance is usually triggered by the touring nurse through short-pressing the white balance function key at the imaging host, or by the assistant through the corresponding key on the camera. The above two operations for functions of the image white balance and turning on the light source have the problem of low efficiency, which increases the inconvenience of use in a very busy preoperative situation.

The existing endoscope imaging system can perform function for image white balance with the help of operating room lighting even when the light source unit is not turned on. However, this function for image white balance lacks the correct brightness coordination of the light source unit, so that a white balance parameter is actually problematic. When the endoscope 111 is used in an abdominal cavity, it can cause abnormal color in the image. Therefore, if the light source unit 130 is forgotten to be turned on before performing the operation of image white balance, and the light source unit 130 is turned on again after the operation of image white balance, the color will be abnormal after the endoscope 111 enters the abdominal cavity, which brings problems to clinical use.

Therefore, in an embodiment, after the function key of the endoscope imaging system is triggered, the image processing unit 120 controls the light source unit 130 to perform a first function of turning on the light source unit 130 and providing the illumination light at a first preset brightness value without delay, after the light source unit 130 is turned on. For example, when the light source unit 130 controls the light source unit 130 to be turned on, the light source unit 130 immediately emits a light with the first preset brightness value. Correspondingly, this function key is a white balance key, and the second function is a function for image white balance of the endoscope imaging system. Wherein, the first preset brightness value is the appropriate brightness value required to achieve the function for image white balance. This embodiment creatively proposes to link the white balance function with the strong light output function of the light source unit, simplifying the steps of turning on the light source, and also satisfying the usage steps of traditional nursing personnel in clinical scenarios.

In this embodiment, the first function includes controlling the light source unit 130 to be turned on, and emit a light at the first preset brightness value without delay after the light source unit 130 is turned on. Wherein, the function for image white balance needs to be achieved, when the light source unit 130 is turned on and the brightness value of the illumination light provided by the light source unit 130 is at an appropriate value. Therefore, the image processing unit 120 controls the light source unit 130 to immediately output a light at the first preset brightness value after the light source unit 130 is controlled to be turned on, so as to achieve a better function for image white balance. When the light source unit 130 emits the light at the first preset brightness value, the function for image white balance which corresponds to the white balance key is controlled to be performed. The first function and the second function in this embodiment are linked functions that have an associated relationship. After the first function is performed, the second function is linked and performed. It should be noted that the steps of turning on of the light source unit and providing the illumination light by the light source can be considered as two separate steps, or as one step of providing the illumination light when turning on the light source unit, depending on the actual application of different embodiments.

In this embodiment, by triggering the white balance key, such as operating the white balance key of the imaging head, the light source unit 130 can be automatically turned on, immediately emit the light at the first preset brightness value for satisfying the function for image white balance, and then the function for image white balance which corresponds to the white balance key can be performed. These functions are implemented by one operation, which reduces clinical operation steps, improves operation efficiency, and avoids the problem of delaying the surgical progress, due to that the touring nurse is busy or the assistant is not familiar with the operation. Moreover, these functions are directly realized through the function key of the imaging head, which is very convenient to use. In addition, it can also avoid image color anomalies caused by performing the function for image white balance when forgetting to turn on the light source unit.

When performing the function for image white balance, if the light source unit 130 does not immediately emit the light at the first preset brightness value after being turned on, but directly links the second function to perform the function for image white balance of the endoscope imaging system; at this time, the illumination light provided by the light source unit 130 does not have an appropriate brightness value required for the function for image white balance. When the second function is linked to be performed, it causes incorrect white balance parameter and problem, which can lead to abnormal color of the endoscope imaging system during use, affect the smooth progress of surgery. Therefore, when the second function which corresponds to the function key is the function for image white balance, it is beneficial for the first function to be that turning on the light source unit and immediately emitting light by the light source unit.

In an embodiment, the image processing unit 120 controls the light source unit 130 to perform a first function of turning on the light source unit 130; and after the light source unit 130 is turned on, controls the light source unit 130 to provide an illumination light with a brightness value thereof being controlled to increase from zero or a first preset brightness value to a second preset brightness value within a preset time length.

In clinical practice, when the light source unit 130 is turned on, the endoscope 111 is still outside the body of the patient. All light source units 130 on the market immediately emit strong light, when the light source units 130 are turned on. If the endoscope 111 is aimed at eyes of clinical personnel at this time, they may not have enough time to react and avoid strong light, which can easily cause eye burns.

In this case, correspondingly, after the function key of the endoscopic imaging system is triggered, the image processing unit 120 controls the light source unit 130 to perform the first function and controls the endoscopic imaging system to perform the second function which corresponds to the function key. Wherein, the first function is controlling the light source unit 130 to be turned on; and after the light source unit 130 is turned on, providing the illumination light which is provided by the light source unit 130, with a brightness value thereof being controlled to increase from zero or a first preset brightness value to a second preset brightness value within a preset time length. Wherein, the triggered function key is any function key which is not a key for white balance, such as a function key which corresponds to a photographing function. The first preset brightness value can be a smaller brightness value, thus reducing the harm caused to user by the strong light after turning on the light source due to improper operation. The second preset brightness value is a larger brightness value, which is suitable for surgery.

In this embodiment, the first function is controlling the light source unit 130 to slowly emit the light after it is turned on, that is, controlling the light source unit 130 to gradually adjust the brightness of the illumination light from weak to strong, so as to reach the second preset brightness value, which can fully give clinical personnel reaction time to avoid strong light, avoid eye discomfort caused by the immediate output of strong light by the light source unit 130, and avoid eye burns.

In an embodiment, the image processing unit 120 controls the light source unit 130 to perform a first function of turning on the light source unit 130, and controls a brightness value of the illumination light which is provided by the light source unit 130 to increase, in a linear or nonlinear manner or with a predetermined step, from zero or the first preset brightness value to the second preset brightness value within the preset time length, after the light source unit 130 is turned on. Wherein increasing with a predetermined step can be understood as increasing the brightness value of the illumination light by a same increment value (preset step).

An embodiment of this disclosure also provides an endoscope imaging system, which has a same structure as the endoscope imaging system mentioned above. Please refer to the description of the corresponding structure mentioned above for details. The difference lies in that the image processing unit 120 preforms different functions. The following describes the differences between the image processing unit 120 in this embodiment and the image processing unit 120 mentioned above. Due to the identical structure, same reference numbers are referenced in followings.

In this embodiment, the image processing unit 120 is still in signal connection with the light source unit 130, for controlling the light source unit 130 to perform the first function after the function key is triggered. The function key is also configured to control the endoscope imaging system to perform the second function which corresponds to the function key, after the function key is re-triggered. The first function includes at least one of: turning on the light source unit, and providing the illumination light. Wherein, the second function is different from the first function. The first function is the function which is performed by the light source unit 130, and the second function is a function which originally corresponds to the function key. In this embodiment, the image processing unit 120 is still in signal connection with the light source unit 130. After the function key is triggered, the light source unit 130 still needs to be controlled to perform the first function, but the second function is only performed after the function key is re-triggered.

In an embodiment, the second function includes one or more of: photographing, video recording, white balance, autofocus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, turning on and off a smoke exhaust.

In an embodiment, the function key is triggered based on a first operation of a user, so as to perform the first function; the function key is re-triggered based on a second operation of a user, so as to perform the second function.

In an embodiment, the first operation is long-pressing the function key by the user, the second operation is short-pressing the function key by the user. The first operation is preset as long-pressing the function key by the user, for considering that if the first function is turning on the light source unit, such operation can try to avoid the user from accidentally touching the function key in the early stage of surgical preparation, which may cause abnormal action to turn on the light source unit. Of course, in other embodiments, the operation can be preset according to actual requirements.

In an embodiment, the first function is: after the light source unit 130 is turned on, providing the illumination light which is provided by the light source unit 130, with a brightness value thereof being controlled to increase from zero or a first preset brightness value to a second preset brightness value within a preset time length; wherein the first preset brightness value is smaller than the second preset brightness value; the function key is any function key which is not a key for white balance. In this embodiment, the specific first function is defined, which is controlling the light source unit 130 to slowly emit the light, after the function key is triggered. Correspondingly, the function key is any function key which is not a key for white balance.

After the function key is triggered, the image processing unit 120 can control the light source unit 130 to perform the first function. The function key is further configured to, when re-triggered during operation of the endoscope imaging system, control to perform the second function which corresponds to the function key. If the function key is a photographing key, the second function is the photographing function. When the photographing key is re-triggered, it controls to perform the photographing function.

In this embodiment, the function key, which is not the key for white balance, is defined. In such a way, after the light source unit 130 is turned on, it slowly lights up. This can fully give clinical personnel reaction time to avoid strong light, avoid eye discomfort caused by the immediate release of strong light by the light source unit 130, and avoid eye burns. In addition, the corresponding control of the light source unit 130 can be achieved by the triggered function key, which key is not the key for white balance, which avoids the problems of affecting the surgical progress, which problems are caused by that the touring nurse is busy before surgery or the assistant is not familiar with the operation, and improves surgical efficiency.

In an embodiment, the image processing unit 120 controls the light source unit 130 to perform a first function of controlling the light source unit 130 to provide an illumination light with a brightness value to increase from zero or the first preset brightness value to the second preset brightness value within the preset time length, in a linear or nonlinear manner, after the light source unit 130 is turned on; or controls the light source unit 130 to perform a first function of controlling the light source unit 130 to provide an illumination light with a brightness value to increase from zero or the first preset brightness value to the second preset brightness value within the preset time length, with a predetermined step, after the light source unit 130 is turned on.

In an embodiment, the image processing unit 120 is further configured to, when determining that light source unit 130 is in a turned-off state, control the light source unit 130 to perform the first function after the function key is triggered, and is further configured to, when determining that light source unit 130 is in a turned-on state, control to directly perform the second function which corresponds to the function key, after the function key is re-triggered. In this embodiment, the triggering manner(s) for the first function and the second function may be the same or different. In an embodiment, the first function can be controlling the light source unit 130 to be turned on; and controlling the light source unit 130 to provide an illumination light with a brightness value thereof being controlled to increase from zero or a first preset brightness value to a second preset brightness value within a preset time length, after the light source unit 130 is turned on. Correspondingly, the function key is any function key which is not a key for white balance.

In this embodiment, when the function key is triggered, whether to control the light source unit 130 to perform the first function, or whether to control to perform the second function which corresponds to the function key, is based on whether the light source unit 130 is turned on. For example, if the light source unit 130 is in a turned-off state, the light source unit 130 is controlled to perform the first function. If the light source unit 130 is in a turned-on state, the second function which corresponds to the function key, is directly controlled to be performed.

An embodiment of this disclosure also provides an endoscope imaging system, which has a same structure as the endoscope imaging system mentioned above. Please refer to the description of the corresponding structure mentioned above for details. The difference lies in that the image processing unit 120 preforms different functions. The following describes the differences between the image processing unit 120 in this embodiment and the image processing unit 120 mentioned above. Due to the identical structure, same reference numbers are referenced in followings.

In this embodiment, the image processing unit 120 is still in signal connection with the light source unit 130. The image processing unit 120 is further configured to perform image recognition based on the image signal which is obtained from the image acquisition unit 110, if the light source unit 130 does not provide the illumination light, and to control the light source unit 130 to perform a first function, when an image recognition result is determined to satisfy a preset scenario; wherein the first function includes at least one of: turning on the light source unit 130, and providing the illumination light. In this embodiment, the image processing unit 120 directly performs image recognition based on the image signal to automatically control the light source unit 130 to perform the first function. Therefore, there is no need for manual operation, and the light source unit 130 is automatically controlled to perform the first function, which improves surgical efficiency and avoids the problem of affecting the surgical progress due to that the touring nurse is busy or the assistant is not familiar with the operation.

In an embodiment, when the image processing unit 120 performs image recognition, if it recognizes that the image corresponding to the image signal includes a calibration version/standard version, it determines that the image recognition result satisfies a first preset scenario, and the light source unit 130 is controlled to perform the first function of turning on the light source unit 130. Wherein, the calibration version/standard version can be white. In this way, an automatic calibration function for image white balance is achieved.

In an embodiment, when the image processing unit 120 performs image recognition, if it recognizes that an imaged part inside the image, which part corresponds to the image signal, is a part inside the body of the patient or is not a part outside the body of the patient, it means that the endoscope 111 is inside the body of the patient. Then, it is determined that the image recognition result satisfies a second preset scenario, that is, when the image recognition result characterizes that the endoscope 111 of the image acquisition unit 110 is inside the body of the patient, the light source unit 130 is controlled to perform the first function of turning on the light source unit 130 for the convenience of surgery.

Figure 4:
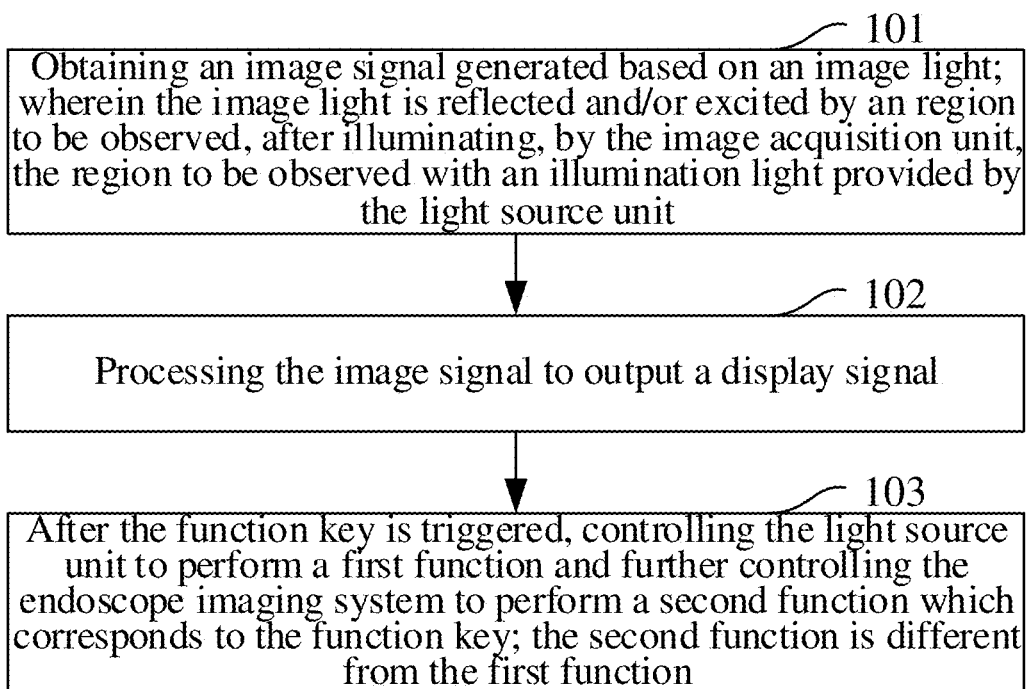
FIG. 4 is a flowchart of a control method for a light source of an endoscope imaging system provided in an embodiment of this disclosure.

As shown in FIG. 4, a flowchart of a control method for a light source of an endoscope imaging system provided in an embodiment of this disclosure, is disclosed. The endoscopic imaging system can be a corresponding endoscopic imaging system described above, and the control method for the light source is specifically applied to the image processing unit 120 of the endoscopic imaging system, including the following steps.

Step 101, the image processing unit obtains an image signal which is generated based on an image light; wherein the image light is reflected and/or excited by a region of a patient to be observed, after illuminating, by the image acquisition unit, the region to be observed with an illumination light which is provided by the light source unit.

The image processing unit 120 obtains the image signal transmitted by the imaging head 112 of the image acquisition unit 110. The image signal is generated based on an image light through the imaging head 112. The image light is reflected and/or excited by a region of a patient to be observed, after illuminating the region to be observed with an illumination light which is transmitted by the light source unit 130 through the endoscope 111. After the imaging head 112 obtains the image signal, it transmits the image signal to the imaging host 121 of the image processing unit 120. Specifically, the connection relationships between the light source unit 130, the image acquisition unit 110, and the image processing unit 120, as well as their specific achievable functions, are described in the corresponding paragraphs above, and are not elaborated here.

Step 102, the image processing unit processes the image signal to output a display signal.

This display signal can be displayed on the display screen.

Step 103, after the function key is triggered, the light source unit is controlled to perform a first function which corresponds to the function key, and the endoscope imaging system is controlled to perform the second function which also corresponds to the function key; wherein the first function and the second function are different.

The imaging host 121 of the image processing unit 120 is in signal connection with the light source unit 130. After the function key of the endoscope imaging system is triggered, the imaging host 121 of the image processing unit 120 is configured to transmit a corresponding first instruction to the light source unit 130, so as to control the light source unit 130 to perform the first function, to transmit a corresponding second instruction to the image acquisition unit 110, such as the imaging head 112, so as to control the endoscope imaging system to perform the second function which corresponds to the function key itself, or control the image processing unit 120 itself to perform the second function, wherein the second function is different from the first function.

In an embodiment, the first function includes at least one of: turning on the light source unit, and providing the illumination light; the second function includes one or more of: photographing, video recording, white balance, autofocus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, turning on and off a smoke exhaust.

In an embodiment, the first function is a function that can only be performed by the light source unit 130.

In an embodiment, the first function and the second function are linked functions with a related relationship. The performing of the first function or of the second function depends on the performing of another function. For example, the performing of the first function requires the performing of the second function as a prerequisite, or the performing of the second function requires the performing of the first function as a prerequisite (i.e., the first function is performed before the second function).

In some embodiments, the first function is performed before the second function.

In an embodiment, the first function is controlling the light source unit 130 to be turned on/of, or turning on/off the light source unit 130.

In an embodiment, the first function is providing the illumination light at a first preset brightness value without delay, after the light source unit 130 is controlled to be turned on. In an embodiment, the function key is a key for white balance, and the second function is a function for image white balance of the endoscope imaging system. Correspondingly, the first preset brightness value is an appropriate brightness value required to achieve the function for image white balance.

In an embodiment, the first function is: after the light source unit 130 is turned on, providing the illumination light which is provided by the light source unit 130, with a brightness value thereof being controlled to increase from zero or a first preset brightness value to a second preset brightness value within a preset time length; wherein the first preset brightness value is smaller than the second preset brightness value, so as to achieve a slow light output. Correspondingly, the function key is any function key which is not a key for white balance.

In an embodiment, the first function is: after the light source unit 130 is turned on, providing the illumination light which is provided by the light source unit 130, with the brightness value thereof being controlled to increase from zero or the first preset brightness value to the second preset brightness value within the preset time length, in a linear or nonlinear manner or with a predetermined step.

In an embodiment, the function key is triggered based on a manual operation of a user; or if the light source unit does not provide the illumination light, the function key is triggered based on a recognition result of the image signal, which signal is obtained by the image processing unit.

In an embodiment, the function key is a physical function key which is arranged at the image acquisition unit 110 (such as a physical function key arranged at the imaging head), or a physical function key which is arranged at the image processing unit 120 and/or a virtual function key which is displayed on a graphic user interface of the image processing unit (such as a physical function key at the imaging host 121 or a virtual function key displayed on the graphic user interface).

In an embodiment, the function key at least one of: a physical function key which is arranged at the image acquisition unit 110, a physical function key which is arranged at the image processing unit 120, or a virtual function key which is displayed on a graphic user interface of the image processing unit 120.

In an embodiment, the function key includes combination key(s), which include(s) multiple keys; the combination key(s) is (are) triggered, after the multiple keys are operated by a user according to a preset rule.

As shown in FIG. 5, a flowchart of a control method for a light source of an endoscope imaging system provided in another embodiment of this disclosure, is disclosed. The control method for the light source is specifically applied to the image processing unit 120 of the endoscopic imaging system, including the following steps.

Step 201, the image processing unit obtains an image signal which is generated based on an image light; wherein the image light is reflected and/or excited by a region of a patient to be observed, after illuminating, by the image acquisition unit, the region to be observed with an illumination light which is provided by the light source unit.

Step 202, the image processing unit processes the image signal to output a display signal.

Step 203, the light source unit is controlled to perform a first function, after the function key is triggered; and a second function which corresponds to the function key, is controlled to be performed, after the function key is re-triggered; wherein the first function and the second function are different.

In an embodiment, the first function includes at least one of: turning on the light source unit, and providing the illumination light.

In an embodiment, the second function includes one or more of: photographing, video recording, white balance, autofocus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, turning on and off a smoke exhaust.

In an embodiment, the first function is a function performed by the light source unit 130, and the second function is a function which originally corresponds to the function key. In this embodiment, the image processing unit 120 is still in signal connection with the light source unit 130. After the function key is triggered, the light source unit 130 still needs to be controlled to perform the first function, but the second function is only performed after the function key is re-triggered.

In an embodiment, the first function is: after the light source unit 130 is turned on, providing the illumination light which is provided by the light source unit 130, with a brightness value thereof being controlled to increase from zero or a first preset brightness value to a second preset brightness value within a preset time length; wherein the first preset brightness value is smaller than the second preset brightness value. Wherein, the function key is any function key which is not a key for white balance.

In an embodiment, the first function is: after the light source unit 130 is turned on; controlling the light source unit 130 to provide the illumination light, with a brightness value thereof being controlled to increase from zero or the first preset brightness value to the second preset brightness value within the preset time length, in a linear or nonlinear manner; or controlling the light source unit 130 to provide the illumination light, with a brightness value thereof being controlled to increase from zero or the first preset brightness value to the second preset brightness value within the preset time length with a predetermined step.

In an embodiment, the function key is triggered based on a first operation of a user, so as to perform the first function; the function key is re-triggered based on a second operation of a user, so as to perform the second function.

In an embodiment, the first operation is long-pressing the function key by the user, the second operation is short-pressing the function key by the user. The first operation is preset as long-pressing the function key by the user, for considering that if the first function is turning on the light source unit, such operation can try to avoid the user accidentally touching the function key in the early stage of surgical preparation, which may cause abnormal action to turn on the light source unit. Of course, in other embodiments, the operation can be preset according to actual requirements.

In an embodiment, after the function key is triggered, if the image processing unit 120 determines that the light source unit 130 is in a turned-off state at this time, it controls the light source unit 130 to perform the first function. When the function key is re-triggered, if the image processing unit 120 determines that the light source unit 130 is already in a turned-on state at this time, it directly controls to perform the second function which corresponds to the function key. In this embodiment, triggering for performing of the first and second functions can be based on the same user operation or different operations. In an embodiment, the first function can be controlling a brightness value of the illumination light which is provided by the light source unit 130 to increase, from zero or a first preset brightness value to a second preset brightness value within a preset time length, after the light source unit 130 is controlled to be turned on. Wherein the first preset brightness value is smaller than the second preset brightness value. Correspondingly, the function key is any function key which is not a key for white balance.

As shown in FIG. 6, a flowchart of a control method for a light source of an endoscope imaging system provided in another embodiment of this disclosure, is disclosed. The control method for the light source is specifically applied to the image processing unit 120 of the endoscopic imaging system, including the following steps.

Step 301, the image processing unit obtains an image signal which is generated based on an image light; wherein the image light is reflected and/or excited by a region of a patient to be observed, after illuminating, by the image acquisition unit, the region to be observed with an illumination light which is provided by the light source unit.

Step 302, the image processing unit processes the image signal to output a display signal.

Step 303, the image processing unit performs image recognition based on the image signal obtained from the image acquisition unit, if the light source unit does not provide the illumination light; and controls the light source unit to perform a first function, when determining that an image recognition result satisfies a preset scenario; wherein the first function includes at least one of: turning on the light source unit, and providing the illumination light.

In this embodiment, the image processing unit 120 is still in signal connection with the light source unit 130. After the function key is triggered, there is no need to trigger the function key or manual operation, the light source unit 130 is automatically controlled to perform the first function, which improves surgical efficiency.

In an embodiment, when the image processing unit 120 performs image recognition, if it recognizes that the image corresponding to the image signal includes a calibration version/standard version, it determines that the image recognition result satisfies a first preset scenario, and the light source unit 130 is controlled to perform the first function of turning on the light source unit 130.

In an embodiment, when the image processing unit 120 performs image recognition, if it recognizes that an imaged part inside the image, which part corresponds to the image signal, is a part inside the body of the patient or is not a part outside the body of the patient, it means that the endoscope 111 is inside the body of the patient. Then, it is determined that the image recognition result satisfies a second preset scenario, that is, when the image recognition result characterizes that the endoscope 111 of the image acquisition unit 110 is inside the body of the patient, the light source unit 130 is controlled to perform the first function of turning on the light source unit 130.

In the embodiments of the control method for the light source of the endoscope imaging system described above, the parts not described in detail can be found in the corresponding description of the endoscope imaging system in the previous text. The beneficial effects that can be achieved can also be found in the beneficial effects described in the previous text, and are not elaborated here.

Ordinary technical personnel in this field can understand that all or part of the steps in various methods of the above embodiments can be completed through instructions (computer programs) or by controlling related hardware through instructions, which instructions can be stored in a computer-readable storage medium and loaded and performed by the processor. For this purpose, an embodiment of this disclosure provides a storage medium, wherein multiple instructions (computer programs) are stored, which can be loaded by a processor to perform the steps of any embodiment of the control method for the light source applied in an endoscopic imaging system as provided in the embodiment of this disclosure.

Wherein, the storage medium can include Read Only Memory (ROM), Random Access Memory (RAM), disk or optical disc, etc.

Due to the instructions (computer programs) stored in the storage medium, it is possible to perform any step in the control method for the light source applied in the endoscopic imaging system provided in the embodiments of this disclosure. Therefore, it is possible to achieve the beneficial effects that can be achieved in any embodiment of the control method for the light source applied in the endoscopic imaging system provided in the embodiments of this disclosure. Please refer to the previous embodiments for more details which are not repeated here.

The above provides a detailed introduction to an endoscope imaging system, a control method for a light source of an endoscope imaging system, and a computer-readable storage medium provided in the embodiments of this disclosure. Specific examples are applied in this disclosure to explain the principles and implementation methods of this disclosure. The above embodiments are only used to help understand the methods and core ideas of this disclosure. Meanwhile, for technical personnel in this field, there may be changes in specific implementation methods and application scope based on the ideas of this application. In summary, the content of this disclosure should not be understood as a limitation on this application.

What is claimed is:

1. An endoscope imaging system, comprising: an image acquisition unit, an image processing unit, a light source unit, and a function key; wherein:

the light source unit is configured to provide an illumination light;

the image acquisition unit is configured to receive the illumination light which is provided by the light source unit and illuminates a region of a patient to be observed, and acquire an image light which is reflected and/or excited by the region to be observed and generate an image signal based on the image light; and the image processing unit is in connection with the image acquisition unit; wherein the image processing unit is configured to obtain the image signal from the image acquisition unit, and process the image signal to output a display signal;

wherein the image processing unit is further in connection with the light source unit;

wherein after the function key is triggered, the image processing unit is further configured to control the light source unit to perform a first function which corresponds to the function key, and control the endoscope imaging system to perform a second function which corresponds to the function key;

wherein the first function comprises at least one of: turning on the light source unit, and providing the illumination light; and the second function comprises one or more of: photographing, video recording, white balance, autofocus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, and turning on and off a smoke exhaust, wherein the first function is: after the light source unit is turned on, to provide the illumination light which is provided by the light source unit, with a brightness value thereof being controlled to increase from zero or from a first preset brightness value to a second preset brightness value within a preset time length.

2. The endoscope imaging system according to claim 1, wherein the first function is performed before the second function.

3. The endoscope imaging system according to claim 1, wherein the first function further comprises: after the light source unit is turned on, to provide the illumination light at the first preset brightness value without delay.

4. The endoscope imaging system according to claim 3, wherein the function key is a key for white balance, and the second function is the white balance.

5. The endoscope imaging system according to claim 1, wherein the first function is: after the light source unit is turned on, to provide the illumination light which is provided by the light source unit, with the brightness value thereof being controlled to increase from zero or from the first preset brightness value to the second preset brightness value within the preset time length, in a linear or nonlinear manner or with a predetermined step.

6. The endoscope imaging system according to claim 1, wherein the function key is not a key for white balance.

7. The endoscope imaging system according to claim 1, wherein, the function key is triggered based on a manual operation of a user; or the function key is triggered based on a recognition result of the image signal which is obtained by the image processing unit, if the light source unit does not provide the illumination light.

8. The endoscope imaging system according to claim 7, wherein the function key comprises at least one of: a physical function key included at the image acquisition unit, a physical function key included at the image processing unit, and a virtual function key displayed on a graphic user interface of the image processing unit.

9. The endoscope imaging system according to claim 1, wherein the function key comprises a combination key having multiple keys; wherein the combination key is triggered, after the multiple keys are operated by a user according to a preset rule.

10. An endoscope imaging system, comprising: an image acquisition unit, an image processing unit, a light source unit, and a function key, wherein:

the light source unit is configured to provide an illumination light;

the image acquisition unit is configured to receive the illumination light which is provided by the light source unit and illuminates a region of a patient to be observed, and acquire an image light which is reflected and/or excited by the region to be observed and generate an image signal based on the image light; and the image processing unit is in connection with the image acquisition unit; wherein the image processing unit is configured to obtain the image signal from the image acquisition unit, and process the image signal to output a display signal;

wherein the image processing unit is further in connection with the light source unit; wherein the image processing unit is further configured to control the light source unit to perform a first function which corresponds to the function key, after the function key is triggered; and to further control the endoscope imaging system to perform a second function which corresponds to the function key, after the function key is re-triggered; wherein the first function comprises at least one of: turning on the light source unit, and providing the illumination light; and the second function is different from the first function, wherein the function key is triggered based on a first operation of a user, so as to perform the first function, and the function key is re-triggered based on a second operation of the user, so as to perform the second function, and wherein the first operation is long-pressing the function key by the user, and the second operation is short-pressing the function key by the user.

11. An endoscope imaging system, comprising: an image acquisition unit, an image processing unit, a light source unit, and a function key, wherein:

the light source unit is configured to provide an illumination light;

the image acquisition unit is configured to receive the illumination light which is provided by the light source unit and illuminates a region of a patient to be observed, and acquire an image light which is reflected and/or excited by the region to be observed and generate an image signal based on the image light; and the image processing unit is in connection with the image acquisition unit; wherein the image processing unit is configured to obtain the image signal from the image acquisition unit, and process the image signal to output a display signal;

wherein the image processing unit is further in connection with the light source unit; wherein the image processing unit is further configured to control the light source unit to perform a first function which corresponds to the function key, after the function key is triggered; and to further control the endoscope imaging system to perform a second function which corresponds to the function key, after the function key is re-triggered; wherein the first function comprises at least one of: turning on the light source unit, and providing the illumination light; and the second function is different from the first function, wherein the function key is a key for white balance; the first function is: after the light source unit is turned on, to provide the illumination light at a first preset brightness value without delay; and the second function is the white balance.

12. An endoscope imaging system, comprising: an image acquisition unit, an image processing unit, a light source unit, and a function key, wherein:

the light source unit is configured to provide an illumination light;

the image acquisition unit is configured to receive the illumination light which is provided by the light source unit and illuminates a region of a patient to be observed, and acquire an image light which is reflected and/or excited by the region to be observed and generate an image signal based on the image light; and the image processing unit is in connection with the image acquisition unit; wherein the image processing unit is configured to obtain the image signal from the image acquisition unit, and process the image signal to output a display signal;

wherein the image processing unit is further in connection with the light source unit; wherein the image processing unit is further configured to control the light source unit to perform a first function which corresponds to the function key, after the function key is triggered; and to further control the endoscope imaging system to perform a second function which corresponds to the function key, after the function key is re-triggered; wherein the first function comprises at least one of: turning on the light source unit, and providing the illumination light; and the second function is different from the first function, wherein the first function is: after the light source unit is controlled to be turned on, to provide the illumination light which is provided by the light source unit, with a brightness value thereof being controlled to increase from zero or from a first preset brightness value to a second preset brightness value within a preset time length; wherein the first preset brightness value is smaller than the second preset brightness value; and the function key is not a key for white balance.

13. The endoscope imaging system according to claim 10, wherein the second function comprises one or more of: photographing, video recording, white balance, autofocus, mode cycling, electronic zooming, brightness adjustment(s) for white light(s), brightness adjustment(s) for fluorescence(s), 3D/2D switching, selection(s) for external input source(s), spectral coloring switching, timer starting, turning on and off a pneumoperitoneum machine, and turning on and off a smoke exhaust.

14. An endoscope imaging system, comprising: an image acquisition unit, an image processing unit, a light source unit, and a function key; wherein:

the light source unit is configured to provide an illumination light;

the image acquisition unit is configured to receive the illumination light which is provided by the light source unit and illuminates a region of a patient to be observed, and acquire an image light which is reflected and/or excited by the region to be observed and generate an image signal based on the image light; and the image processing unit is in connection with the image acquisition unit; wherein the image processing unit is configured to obtain the image signal from the image acquisition unit, and process the image signal to output a display signal;

wherein the image processing unit is further in connection with the light source unit; wherein the image processing unit is further configured to control the light source unit to perform a first function, and control the endoscope imaging system to perform a second function which corresponds to the function key, after the function key is triggered; wherein the first function is different from the second function, wherein the first function is: after the light source unit is turned on, to provide the illumination light which is provided by the light source unit, with a brightness value thereof being controlled to increase from zero or from a first preset brightness value to a second preset brightness value within a preset time length; wherein the function key is not a key for white balance.

15. The endoscope imaging system according to claim 14, wherein the first function further comprises: after the light source unit is turned on, to provide the illumination light at the first preset brightness value without delay.

16. The endoscope imaging system according to claim 14, wherein the function key is a physical function key included at the image acquisition unit.

17. The endoscope imaging system according to claim 14, wherein the function key is a single key, and the image processing unit is specifically configured to control the light source unit to perform the first function, and control the endoscope imaging system to perform the second function which corresponds to the function key, after the single key is triggered.

18. The endoscope imaging system according to claim 14, wherein the second function is automatically performed after the first function.

19. The endoscope imaging system according to claim 14, wherein the function key comprises a combination key having one or more keys; wherein the function key is triggered, after the one or more keys are operated by a user according to a preset rule, so as to perform the first function and the second function.

* * * * *